(12) United States Patent
Trimboli et al.

(10) Patent No.: US 7,956,040 B2
(45) Date of Patent: Jun. 7, 2011

(54) COMBINATION OF CATECHIN AND QUERCETIN FOR PHARMACEUTICAL OR DIETARY USE

(75) Inventors: Domenico Trimboli, Rome (IT); Valter Gatti, Milan (IT); Gian Carlo Naccari, Monza (IT)

(73) Assignee: Giuliani International Limited, Dublin (IE)

( * ) Notice: Subject to any disclaimer, the term of this patent is extended or adjusted under 35 U.S.C. 154(b) by 442 days.

(21) Appl. No.: 10/398,536

(22) PCT Filed: Oct. 11, 2001

(86) PCT No.: PCT/EP01/11779
§ 371 (c)(1),
(2), (4) Date: Aug. 14, 2003

(87) PCT Pub. No.: WO02/34262
PCT Pub. Date: May 2, 2002

(65) Prior Publication Data
US 2004/0014686 A1 Jan. 22, 2004

(30) Foreign Application Priority Data
Oct. 25, 2000 (IT) .................................. MI00A2312

(51) Int. Cl.
*A61K 31/353* (2006.01)
(52) U.S. Cl. ......................................... 514/27; 424/766
(58) Field of Classification Search .................... 514/27; 424/766
See application file for complete search history.

(56) References Cited

U.S. PATENT DOCUMENTS 6,030,621 A * 2/2000 De Long et al. .............. 424/752
6,054,128 A * 4/2000 Wakat .......................... 424/765
6,297,218 B1 * 10/2001 Morazzoni et al. ............. 514/25
6,358,539 B1 * 3/2002 Murad .......................... 424/725
6,569,446 B1 * 5/2003 Howard ........................ 424/442

FOREIGN PATENT DOCUMENTS

WO        WO 98/30228       7/1998

OTHER PUBLICATIONS

Pignatelli et al. The flavonoids quercetin and catechin synergistically inhibit platelet function by antagonizing the intracellular production of hydrogen peroxide1. Am J Clin Nutr. Nov. 2000;72(5):1150-5.*
EP Search Report, (2002).
Database WPI, 1977 Derwent Publications Ltd. London, GB; An 1977-85942y XP-002167241.
Chemical Abstracts, vol. 121, No. 14 Oct. 3, 1994, Columbus Ohio.
Database WPI, 1994 Derwent Publications Ltd. London, GB; An 1994-121162 XP-002167242.
A.S. Meyer, M. Heinonen E.N. Frankel: Food Chemistry vol. 61, No. 1-2, 1998, pp. 71-75 XP-000993315.
Clinical Research V. 42 No. 2 (1994).
Medicine, V. 65 No. 4 pp. 242-267 (1986).
New England Journal of Medicine V. 329, No. 25 (1829-1834), (1993).
Am J. Clin Nutr. 1998; 67; 255-262.

* cited by examiner

*Primary Examiner* — Jake M. Vu
(74) *Attorney, Agent, or Firm* — Hedman & Costigan, P.C.; James V. Costigan; Kathleen A. Costigan

(57) ABSTRACT

The invention relates to a composition for pharmaceutical or dietary use that possesses antioxidant activity and characterized in that it contains as active principle a combination of catechin quercetin, which exert a synergistic action when combined in mutual molar ratios selected within a critical range, from 6:1 to 3:1 mol of catechin:quercetin.

3 Claims, 5 Drawing Sheets

COMBINATION OF CATECHIN AND QUERCETIN FOR PHARMACEUTICAL OR DIETARY USE

Figure 1:
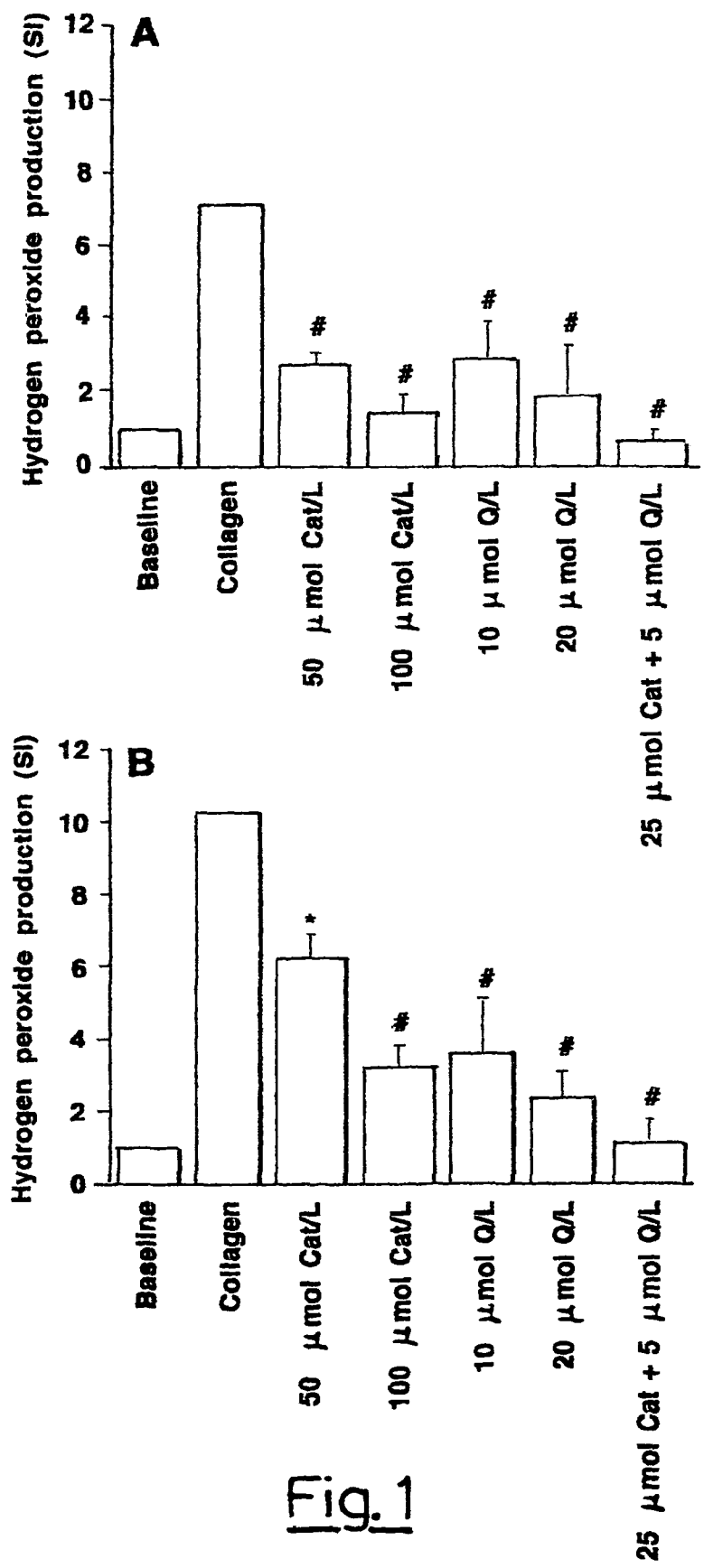

It is known that moderate consumption of red wine is associated with a decreased incidence of cardiovascular events (More, Medicine 1986:65:245-67; Graziano, N. Engl. J. Med. 1993:329:1829-34). Constituents of red wine such as flavonoids have been considered to be involved in the aforementioned beneficial effects on the cardiovascular system on account of their ability to inhibit platelet function. Indeed, experimental studies in vivo on animals demonstrated that both red wine and grape juice reduced platelet activation in canine coronary arteries affected by stenosis. A similar effect was observed with flavonoids isolated from red wine, including quercetin, indicating that these constituents of red wine were involved in eliminating the reduction in flow caused by platelet aggregation (Slane, Clin. Res. 1994; 42; 169A (abstr.)). Several studies in vitro have demonstrated that flavonoids such as resveratrol, quercetin and catechin inhibit platelet aggregation; however, one potential limitation of these studies arises from the fact that the concentration employed to obtain this inhibition was too high. Accordingly, some authors have called into question the antiplatelet activity exerted in vivo by these constituents of red wine (Janssen, Am. J. Clin. Nutr. 1998; 67; 255-62). It should be noted that research into the effects of flavonoids on platelet function has until now focused on each component considered individually; there has never been an investigation of whether the flavonoids can act in combination to inhibit platelet activation. Following the consumption of red wine, more than one flavonoid is circulating in the human body, so such a synergy might be relevant, in that lower concentrations of flavonoids than those studied previously might modulate platelet activity.

Another question concerning the antiplatelet effect of the flavonoids is their mechanism of action. Although the results of the majority of studies are in agreement that the flavonoids interact with the metabolism of arachidonic acid, thus inhibiting the production of thromboxane $A_2$, the mechanism on which this action is based has never been studied. The flavonoids are phenolic compounds whose antioxidant effects are correlated with the deoxidation of radicals rather than with chelation of the metal. It has been suggested that inhibition both of platelet function and of metabolism of arachidonic acid depends on the antioxidant activity, but no study envisaged investigations to discover whether the flavonoids interact with platelet activation by contrasting the effect of oxidizing species formed in situ. The present invention was therefore based on investigating whether the flavonoids, or some of them selectively, could act synergistically to inhibit platelet function, and to interfere with platelet function on the basis of an antioxidant effect.

As a result of this study, the present invention proposes a composition for pharmaceutical or dietary use that possesses high antioxidant activity, characterized in that this active principle comprises a combination of catechin and quercetin in the molar ratio in the range between approx 6:1 and 3:1, respectively.

According to the invention, it has in fact been found, surprisingly, that these two specific flavonoids combined in the said concentration ratios are able to exert their antioxidant activity synergistically.

For a better understanding of the characteristics and advantages of the invention, the details of the study that led to it are now described.

Subjects and Methods

Materials $^{32}$Pi and [$^3$H]oleic acid were from Amersham (Arlington Heights, Ill.). Fura 2/AM and 2',7'-dichlorofluorescein diacetate (DCFH-DA) were from Molecular Probes (Eugene, Oreg.) and Sepharose 2B was from Pharmacia (Uppsala, Sweden). The tetrapeptide Arg-Gly-Asp-Ser (RDGS) was from Bachem Feinchemikalien AG (Budendorf, Switzerland). The type 1 collagen was from Mascia Brunelli (Milan, Italy). The HPLC columns (Partisil 10 SAX) were from Whatman (Clifton, N.J.). The bovine serum albumin, HEPES, acetylsalicylic acid, catechin, quercetin, fibrinogen, inorganic pyrophosphatase, digitonin, formaldehyde, indomethacin, phosphocreatine and creatine kinase were from Sigma Chemical Co. (St. Louis).

Platelet Preparations

Drug-free human blood obtained from healthy volunteers was coagulated with acid:citrate:dextrose. Platelet-rich plasma was centrifuged at 800×g for 20 min at room temperature and the pellet was suspended in a volume equal to half the initial volume of autologous plasma, low in platelets. The platelet suspensions were incubated for 1 h at 37° C. with 3 µmol of Fura 2/AM per L, 40 µmol DCFH-DA/L, 7.4 GBq (2 Ci) $^{32}$Pi/L, or 3.7 MBq (1 mCi) [$^3$H]oleic acid/L. The platelets were washed by exclusion chromatography on Sepharose 2B using a $Ca^{2+}$-free Tyrodes buffer (134 mmol NaCl/L, 2.9 mmol KCl/L, 0.34 mmol $Na_2HPO_4$/L and 2 mmol $MgCl_2$/L) containing 0.2% of bovine serum albumin, 5 mmol glucose/L and 10 mmol HEPES/L, pH 7.35. The platelets that had been submitted to exclusion chromatography (PSEC) were adjusted to a final concentration of $2 \times 10^{11}$ cells/L. Since the addition of methanol to the suspensions of PSEC at concentrations<0.5% did not cause any change in the response of the PSEC to collagen, this ratio was used for obtaining final concentrations of quercetin that varied between 5 and 20 µmol/L. Catechin and quercetin were added to the suspensions of PSEC while stirring continuously for 30 min at 37° C. and then removed by centrifugation at 800×g for 20 min at room temperature.

Analysis of Platelet Flow and Aggregation by Cytometry

DCFH-DA was added to the PSEC (final concentration: 40 µmol/L); after 15 minutes of incubation with or without catechin or quercetin, the PSEC were activated with collagen. The reaction was stopped with 2 mmol EGTA/L after 1 min. The samples were analysed in a Coulter XL-MCL flow cytometer (Hialeah, Fla.) equipped with an argon laser (emission 480 nm) set up for measuring the logarithmic diffusion of direct light, which is a measure of the dimensions of the particle; logarithmic diffusion of light at 90°, which is a measure of the granularity of the cell; and green fluorescence (DCF) 510-550 nm. The fluorescence signal generated by the probe was expressed as the stimulation index, i.e. intensity of mean channel fluorescence of the stimulated platelets/intensity of mean channel fluorescence of the unstimulated platelets. Platelet aggregation in vitro was evaluated according to Born. The collagen was used at concentrations of 2-4 mg/L.

Concentrations of Cytosol Platelet $Ca^{2+}$

The concentrations of cytosol platelet $Ca^{2+}$ were measured using the fluorescent indicator dye Fura 2, according to Grynkiewicz et al.; the changes in fluorescence were then monitored with a fluorimeter SFM 25 (Kontron, Zurich, Switzerland) set at emission wavelength of 510 nm and excitation wavelength of 340 nm.

Activation of Phospholipase C-Platelet Adhesion to Collagen

The production of 1,3,4-inositol triphosphate ($IP_3$, an indicator of activation of phospholipase C, was analysed 30 s after platelet activation according to Pulcinelli et al. *J. Chromatogr.* 1992,575:51-5. The collagen was used at a concentration of 10 mg/L, which was the lowest concentration capable of inducing a reproducible response. The platelet suspensions identified with [$^3$H]oleic acid were used for evaluating platelet adhesion to collagen (50 mg/L) according to Smith and Dangelmaier.

Statistical Analysis

The data are given as mean values±SEM. The responses in different experimental conditions were compared using the Student t test and the Bonferroni test for evaluating the specific differences between the groups. The significance level was set at P<0.05. Analysis was effected using STATVIEW (Abacus Concepts Inc., Berkeley, Calif.).

The results of the study will now be discussed, with particular reference to FIGS. 1 to 5 in the appended drawings, which show the following diagrams.

FIG. 1 Mean production (±SEM) of hydrogen peroxide in platelets loaded with dichlorofluorescein diacetate at the reference line, after stimulation with collagen alone, and after stimulation with 10 mg of collagen/L (A) or 20 mg of collagen/L (B) with catechin alone (Cat; 50 and 100 µmol/L), quercetin alone (Q; 10 and 20 µmol/L), and a combination according to the invention of catechin (Cat)+quercetin (Q) in 5:1 ratio, i.e. Cat (25 µmol/L)+Q (5 µmol/L). The results were determined by cytofluorimetry, n=5 tests. SI, stimulation index. *,#Significantly different relative to collagen alone: *P<0.05, #P<0.01.

Figure 2:
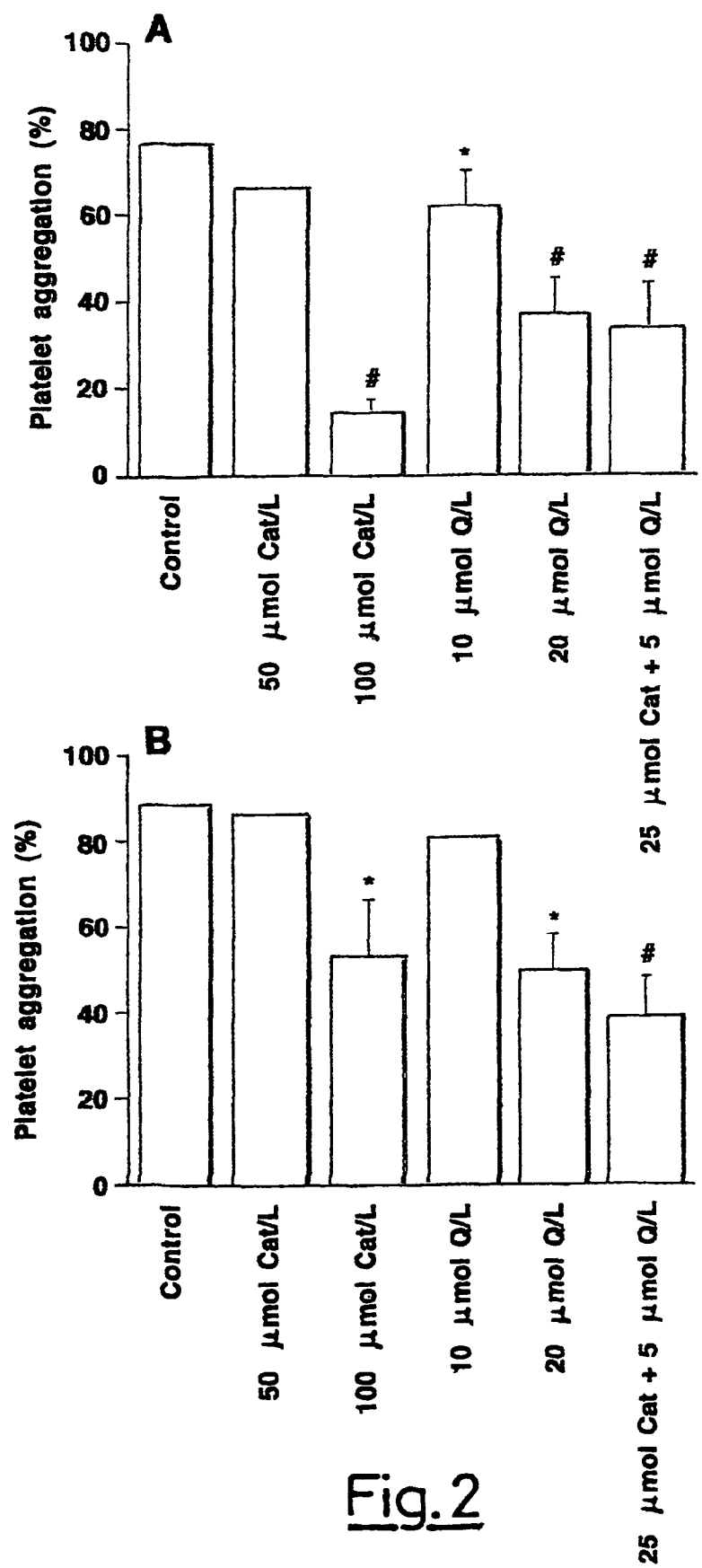

FIG. 2 Mean platelet aggregation (±SEM) at the reference line, after stimulation with collagen alone, and after stimulation with 2 mg of collagen/L. (A) or 4 mg of collagen/L (B) with catechin (Cat; 50 and 100 µmol/L), quercetin (Q; 10 and 20 µmol/L), or Cat (25 µmol/L)+Q (5 µmol/L). n=5 tests. *,#Significantly different relative to collagen alone: *P<0.05, #P<0.01.

Figure 3:
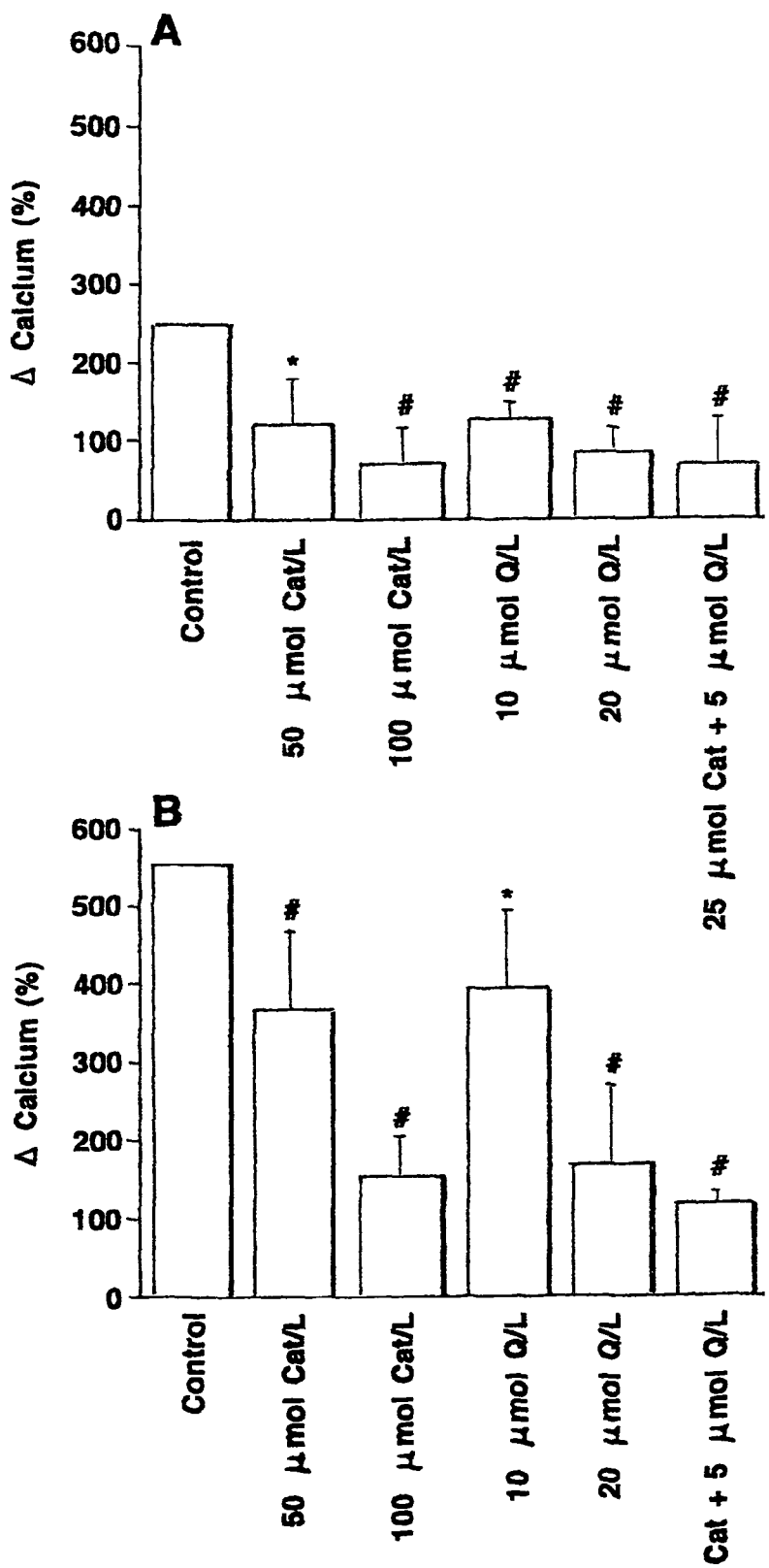

FIG. 3 Mean value (±SEM) of the percentage changes (Δ) in the concentrations of intraplatelet calcium at the reference line, after stimulation with collagen alone, and after stimulation with 4 mg of collagen/L (A) or 8 mg of collagen/L (B) with catechin (Cat; 50 and 100 µmol/L), quercetin (Q; 10 and 20 µmol/L), or Cat (25 µmol/L)+Q (5 µmol/L). n=5 tests. *,#Significantly different relative to collagen alone: *P<0.05, #P<0.01.

Figure 4:
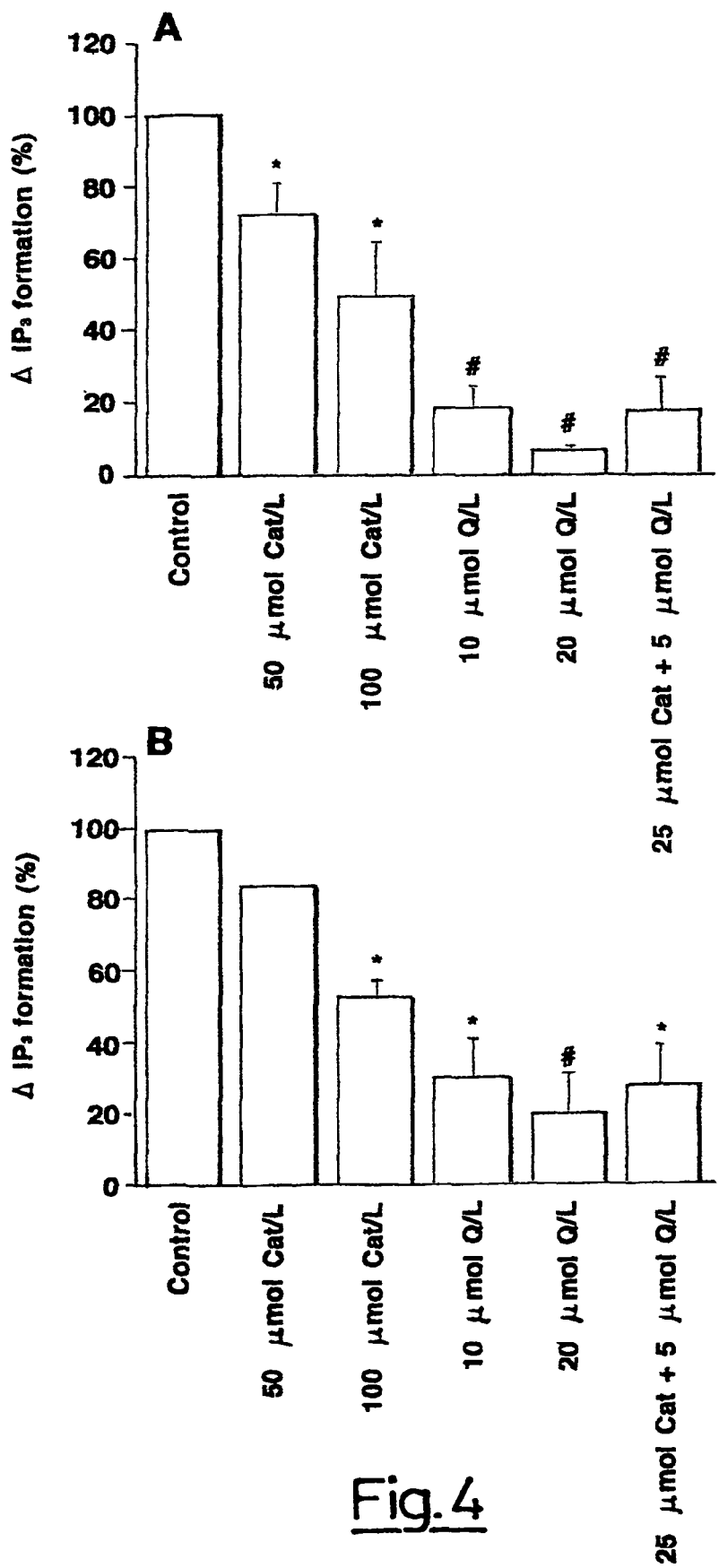

FIG. 4 Mean value (±SEM) of the percentage changes (Δ) in the formation of 1,3,4-inositol triphosphate ($IP_3$) in the platelets at the reference line, after stimulation with collagen alone, and after stimulation with 10 mg of collagen/L (A) or 20 mg of collagen/L (B) with catechin (Cat; 50 and 100 µmol/L), quercetin (Q; 10 and 20 µmol/L), or Cat (25 µmol/L)+Q (5 µmol/L). n=5 tests. *,#Significantly different relative to collagen alone: *P<0.05, #P<0.01.

Figure 5:
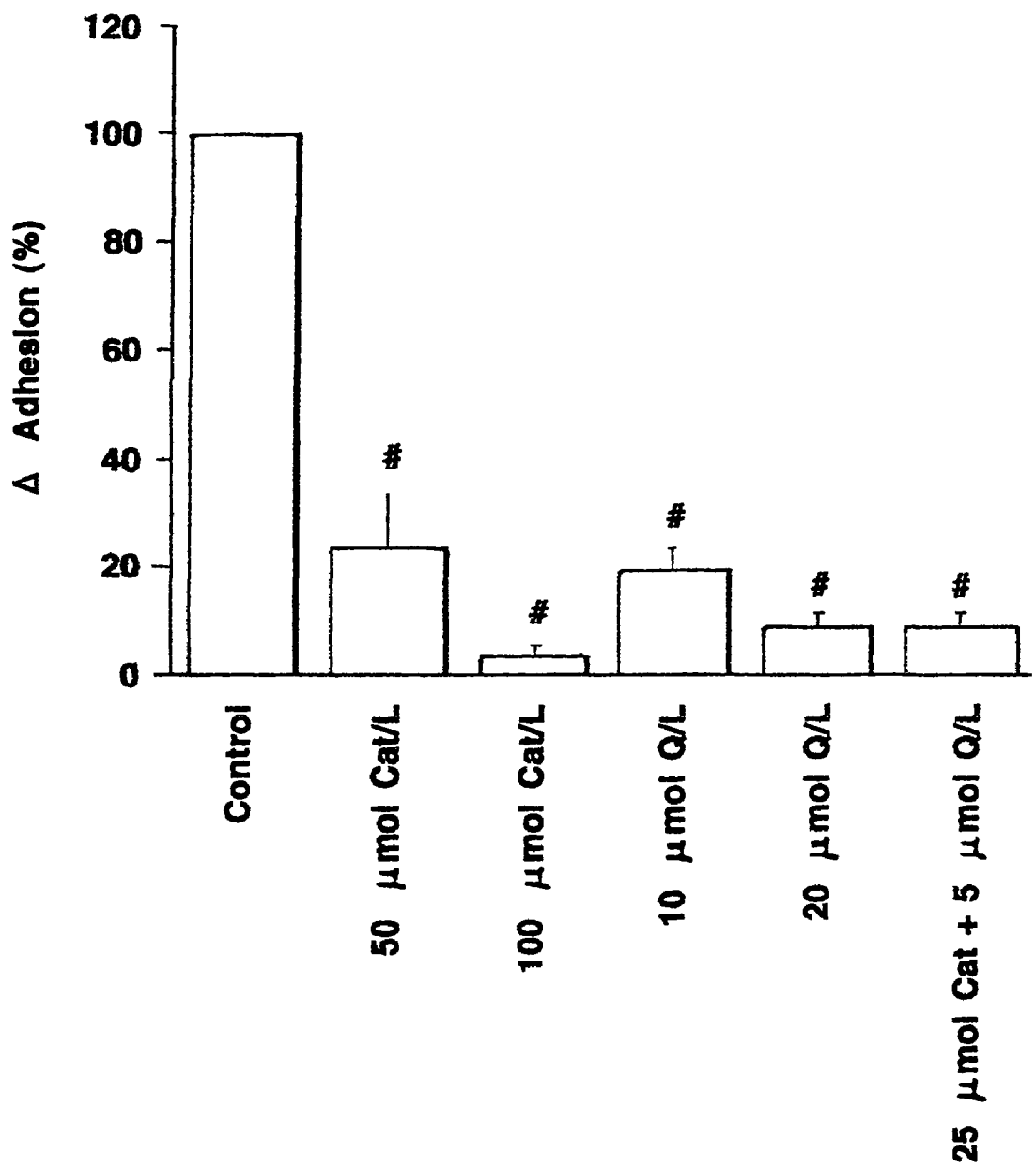

FIG. 5 Mean value (±SEM) of the percentage changes (A) in platelet adhesion to collagen at the reference line, after stimulation with collagen alone, and after stimulation with 50 mg of collagen/L with catechin (Cat; 50 and 100 µmol/L), quercetin (Q; 10 and 20 µmol/L), or Cat (25 µmol/L)+Q (5 µmol/L). n=5 tests. #Significantly different relative to collagen alone: P<0.01.

Results

Analysis by Flow Cytometry

Flow cytometry makes use of the properties of DCFH-DA, which diffuses rapidly through the cellular membranes and is then trapped inside the cell through a reaction of deacetylation. In the presence of hydrogen peroxide, this compound is oxidized to dichlorofluorescein (DCF), which is highly fluorescent. The effect of scalar concentrations of quercetin and catechin on the production of hydrogen peroxide induced by 10 and 20 mg of collagen/L is shown in FIG. 1. Compared with untreated platelets, the platelets stimulated with collagen increased the production of hydrogen peroxide, which depended on the concentration of collagen used. Catechin and quercetin inhibited the production of hydrogen peroxide caused by the collagen on the part of the platelets. The combination of 5 µmol of quercetin/L and 25 µmol of catechin/L gave a significant reduction in formation of hydrogen peroxide caused by 10 and 20 mg of collagen/L; neither of the two compounds alone at such low quantities is reported to have had any inhibitory effect.

Platelet Aggregation

The effect of catechin and quercetin on platelet aggregation was measured using two different concentrations of collagen. Both catechin and quercetin inhibited platelet aggregation caused by collagen. The degree of inhibition depended on the concentration of collagen used. Thus, 100 µmol of catechin/L inhibited ≈75% of platelet aggregation induced by 2 mg of collagen/L and inhibited ≈39% of platelet aggregation induced by 4 mg of collagen/L. In platelets treated with 20 µmol of quercetin/L, the degree of inhibition of platelet aggregation induced by collagen (2 and 4 mg/L) was 50% and 43% respectively. The combination of 25 µmol of catechin/L and 5 µmol of quercetin/L, which had no influence on platelet aggregation when used on their own, produced significant (55%) inhibition of platelet aggregation induced by both the concentrations of collagen (FIG. 2).

Changes in Intracellular Calcium Concentration

Catechin and quercetin inhibited the mobilization of calcium, expressed as a percentage change in the concentration of intracellular calcium. In the platelets stimulated with 4 mg of collagen/L, 100 µmol of catechin/L and 20 µmol of quercetin/L produced a significant decrease in calcium mobilization, of 71% and 65% respectively.

Incubation of the platelets with 25 µmol of catechin/L plus 5 µmol of quercetin/L according to the invention produced a significant inhibition of calcium mobilization of 71%. A similar result was also observed when calcium mobilization was induced by 8 mg of collagen/L (FIG. 3).

Activation of Phospholipase C

Production of [$^{32}$P]$IP_3$ in platelets stimulated by collagen was inhibited by catechin and quercetin: 10 mg of collagen/L, 100 µmol of catechin/L and 20 µmol of quercetin/L caused a significant decrease in $IP_3$ production, of 50% and 93% respectively. Incubation of the platelets with 25 µmol of catechin/L plus 5 µmol of quercetin/L according to the invention caused a significant inhibition of $IP_3$ production of 72%; similar effects were observed when the platelets were stimulated with 20 mg of collagen/L (FIG. 4), but the degree of inhibition was lower, though still significant.

Platelet Adhesion to Collagen

The activation of platelets by collagen is a multistage process. Thus, after being attached initially to the platelets via the pathways of the second messenger, collagen stimulates the release of thromboxane and ADP, which are important platelet agonists that induce aggregation. To study the adhesion of the platelets to collagen (50 mg/L) without the interference of aggregation and of the activation induced by all the known agonists released by the platelet granules on stimulation by collagen, the platelets were subjected to preincubation with aspirin, a cyclooxygenase inhibitor, with the ADP removal system phosphocreatine and creatine kinase, and with the fibrinogen-fibronectin antagonist RDGS (13).

The adhesion of the platelets to 50 µmol of collagen/L in the presence of catechin (50 and 100 µmol/L), quercetin (10 and 20 µmol/L), and catechin (25 µmol/L) plus quercetin (5 µmol/L) according to the invention is presented in FIG. 5. Catechin or quercetin on their own inhibited platelet adhesion to collagen, which was suppressed significantly by 100 µmol catechin/L and 20 µmol quercetin/L. Incubation of the platelets with 25 µmol of catechin/L plus 5 µmol of quercetin/L produced significant inhibition of platelet adhesion of 85%.

The following general conclusions can be drawn from the study described above.

As already mentioned, in the prior art the relationship between consumption of red wine and inhibition of platelet function has been observed in various experimental studies. In fact, intragastric administration of 4.0 mL of red wine/kg of body weight suppressed platelet activation completely in a canine model of coronary stenosis. Although the concentrations of flavonoids in the peripheral blood have not been measured after the administration of red wine, other studies on the same experimental model showed that the flavonoids inhibited platelet activation, thus suggesting their possible involvement in the inhibition of platelet function. According to the study of the present invention, incubation of the platelets with 5 µmol of quercetin/L plus 20 µmol of catechin/L, which had no effect on platelet function individually at these concentrations, is associated with significant inhibition of platelet activation. It should be pointed out that although stimulation was carried out with high concentrations of collagen (8-20 mg/L), necessary for identifying the mobilization of calcium and the production of $IP_3$, the combination of quercetin and catechin inhibits platelet function in every case.

The combination of catechin and quercetin causes even more profound effects on platelet adhesion, which is suppressed almost completely when the platelets are treated according to the invention. In view of the biological importance of platelet adhesion to collagen in the initiation and progression of the arteriosclerotic process, the invention is expected to be useful in particular in the treatment or prevention of cardiovascular disorders (arteriosclerosis, thrombosis, infarction, etc.), for improving cerebral functionality, and for treating mental deterioration in old age.

Other useful indications, based fundamentally on the antioxidant and free-radical-scavenging activity of the active principle, comprise those for the treatment or prevention of cellulite, skin ageing and wrinkles, hair loss, for counteracting the action of UV radiation and of environmental pollutants.

As an overall conclusion, the invention demonstrates that the flavonoids quercetin and catechin act synergistically according to the concentrations indicated for inhibiting platelet adhesion to collagen and platelet aggregation caused by collagen, opposing the intracellular production of hydrogen peroxide.

Non-limiting examples of practical application of pharmaceutical or dietary compositions according to the present invention are now described.

It should be explained that, still in a non-limiting manner, these examples relate to an active principle consisting of a catechin-quercetin combination in molar ratio of approx 5:1.

In particular, the said combination of the two flavonoids, called "complex" in the examples, is obtained according to the examples from an extract of parts, such as seeds and leaves, of *Vitis vinifera* containing approx. 7.5 g of catechin and 1.5 g of quercetin per 100 g of extract. These compositions are preferably taken on a full stomach to optimize the bioavailability of the active principle.

Example 1

Dietary Product for Preventing and Combating Cellulite

Soft Gelatin Capsules

| Composition Each soft gelatin capsule (pearl) contains: | |
|---|---|
| Catechin + Quercetin complex | 60 mg |
| *Ginkgo biloba* dry extract with 24% of ginkgoflavonglucosides | 15 mg |
| *Centella asiatica*, triterpene fraction | 10 mg |
| *Orthosiphon stamineus*, dry extract | 75 mg |
| *Fucus vesiculosus* with 0.1 % of iodine | 100 mg |
| Linden sapwood | 50 mg |
| Chromium-containing yeast | 12.5 mg |
| (equal to chromium | 0.015 mg) |
| Vitamin E acetate | 7.5 mg |
| Soya oil | 290 mg |
| Soya lecithin | 5 mg |
| Mono- and diglycerides of fatty acids | 30 mg |
| Gelatin | 144 mg |
| Glycerol | 66 mg |
| Iron oxide | 0.3 mg |
| Titanium dioxide | 2.3 mg |
| *Clorofilia rameica* | 0.5 mg |

Example 2

Dietary Product for Preventing and Combating Cellulite

Sachets to be Dissolved in Water

| Composition Each sachet contains: | |
|---|---|
| Catechin + Quercetin complex | 100 mg |
| *Ginkgo biloba* dry extract with 24% of ginkgoflavonglucosides | 15 mg |
| *Centella asiatica*, triterpene fraction | 10 mg |
| *Orthosiphon stamineus*, dry extract | 100 mg |
| *Fucus vesiculosus* at 0.1% of iodine | 100 mg |

| Composition Each sachet contains: | |
|---|---|
| Linden sapwood | 100 mg |
| Chromium-containing yeast | 12.5 mg |
| (equal to chromium | 0.025 mg) |
| Vitamin E acetate | 7.5 mg |
| Maltodextrin | 2000 mg |
| Sodium citrate | 360 mg |
| Citric acid monohydrate | 200 mg |
| Tropical aroma | 120 mg |
| Sour cherry aroma | 60 mg |
| *Colloidal silica* | 70 mg |
| Acesulfame K | 8 mg |
| Aspartame | 33 mg |

Example 3

Product for Reinforcing the Hair and Reducing Hair Loss

Soft Gelatin Capsules

| Composition Each soft gelatin capsule (pearl) contains: | |
|---|---|
| Catechin + Quercetin complex | 60 mg |
| Methylsulphonylmethane | 100 mg |
| Vitamin C | 45 mg |
| Vitamin E acetate | 7.5 mg |
| Zinc (as amino acid chelate) | 3.75 mg |
| Copper (as amino acid chelate) | 0.625 mg |
| Vitamin B6 | 1.0 mg |
| Calcium pantothenate | 4.5 mg |
| Folic acid | 0.15 mg |
| Biotin | 0.075 mg |
| Spermidine | 0.25 mg |
| Soya oil | 290 mg |
| Soya lecithin | 5 mg |
| Mono- and diglycerides of fatty acids | 30 mg |
| Gelatin | 145 mg |
| Glycerol | 65 mg |
| Titanium dioxide | 2.8 mg |
| Iron oxide | 0.1 mg |
| *Clorofilla rameica* | 0.6 mg |

Example 4

Composition for Preventing Cardiovascular Diseases

Soft Gelatin Capsules

| Composition Each soft gelatin capsule (pearl) contains: | |
|---|---|
| Catechin + Quercetin complex | 100 mg |
| Ubidecarenone | 10 mg |
| Carnitine | 100 mg |
| Eicosapentaenoic acid (EPA) | 300 mg |
| Docosahexaenoic acid (DHA) | 200 mg |
| Lutein | 2 mg |
| 5-Methyltetrahydrofolic acid | 010 mg |
| Soya oil | 250 mg |
| Soya lecithin | 10 mg |
| Mono- and diglycerides of fatty acids | 40 mg |
| Gelatin | 150 mg |
| Glycerol | 70 mg |
| Titanium dioxide | 2.5 mg |
| Iron oxide | 0.2 mg |
| Ladybird Red | 0.5 mg |

Example 5

Dietary Product for Preventing Skin Ageing and Wrinkles

Soft Gelatin Capsules

| Composition Each soft gelatin capsule (pearl) contains: | |
|---|---|
| Catechin + Quercetin complex | 100 mg |
| Lysine hydrochloride | 125 mg |
| Vitamin C | 45 mg |
| Methylsulphonylmethane | 100 mg |
| Vitamin E acetate | 7.5 mg |
| Copper (as amino acid chelate) | 0.625 mg |
| Zinc (as amino acid chelate) | 3.75 mg |
| Biotin | 0.075 mg |
| Soya oil | 290 mg |
| Soya lecithin | 5 mg |
| Mono- and diglycerides of fatty acids | 30 mg |
| Gelatin | 145 mg |
| Glycerol | 67 mg |
| Titanium dioxide | 2.5 mg |
| Iron oxide | 0.4 mg |

Example 6

Dietary Product for Improving Cerebral Functionality And Preventing Mental Deterioration in Old Age

Soft Gelatin Capsules

| Composition Each soft gelatin capsule (pearl) contains: | |
|---|---|
| Catechin + Quercetin complex | 100 mg |
| Huperzine | 0.050 mg |
| Phosphatidylserine | 50 mg |
| *Ginkgo biloba* extract with 24% of ginkgoflavonglucosides | 15 mg |
| Vitamin B1 | 1.0 mg |
| Vitamin B6 | 1.0 mg |
| Vitamin B12 | 0.001 mg |
| Vitamin C | 90.0 mg |
| Vitamin E acetate | 7.5 mg |
| Zinc (as amino acid chelate) | 3.75 mg |
| Copper (as amino acid chelate) | 0.625 mg |
| Soya oil | 250 mg |
| Soya lecithin | 10 mg |
| Mono- and digycerides of fatty acids | 40 mg |
| Gelatin | 145 mg |
| Glycerol | 67 mg |
| Titanium dioxide | 1.5 mg |
| Iron oxide | 0.2 mg |
| Blue Patent V | 0.5 mg |

Other suitable pharmaceutical or dietary forms according to the invention can be selected from a wide range, which includes every suitable oral form such as tablets, granules, powders and others.

The invention claimed is:

1. A oral composition in the form of a tablet or capsule for pharmaceutical or dietary use, said composition possessing antioxidant activity and characterized in that it contains as an active principle a combination of catechin and quercetin in a molar ratio of 5:1.

2. A composition as defined in claim 1 wherein the active principle contains 7.5 g of catechin and 1.5 g of quercetin per 100 g.

3. A oral composition in the form of a tablet or capsule for pharmaceutical or dietary use, said composition possessing antioxidant activity and characterized in that it contains as an active principle a combination consisting of catechin and quercetin in a molar ratio of 5:1.

* * * * *